United States Patent
Yamamoto et al.

(10) Patent No.: US 10,329,631 B2
(45) Date of Patent: Jun. 25, 2019

(54) CONSTITUTIVE 1,4-DIOXANE-DEGRADING BACTERIA

(71) Applicant: TAISEI CORPORATION, Shinjuku-ku, Tokyo (JP)

(72) Inventors: Norifumi Yamamoto, Tokyo (JP); Yuji Saito, Tokyo (JP); Hironori Taki, Tokyo (JP)

(73) Assignee: TAISEI CORPORATION, Tokyo (JP)

( * ) Notice: Subject to any disclaimer, the term of this patent is extended or adjusted under 35 U.S.C. 154(b) by 0 days.

(21) Appl. No.: 15/573,401

(22) PCT Filed: Apr. 25, 2016

(86) PCT No.: PCT/JP2016/062871
§ 371 (c)(1),
(2) Date: Nov. 10, 2017

(87) PCT Pub. No.: WO2016/181802
PCT Pub. Date: Nov. 17, 2016

(65) Prior Publication Data
US 2018/0135141 A1 May 17, 2018

(30) Foreign Application Priority Data

May 11, 2015 (JP) ................................ 2015-096577
Oct. 19, 2015 (JP) ................................ 2015-205643

(51) Int. Cl.
| | | |
|---|---|---|
| C12N 1/20 | (2006.01) | |
| C12R 1/01 | (2006.01) | |
| B09C 1/10 | (2006.01) | |
| C02F 3/00 | (2006.01) | |
| C07C 43/13 | (2006.01) | |
| A62D 3/02 | (2007.01) | |
| C07D 319/10 | (2006.01) | |
| A62D 101/28 | (2007.01) | |

(52) U.S. Cl.
CPC .................. C12R 1/01 (2013.01); A62D 3/02 (2013.01); B09C 1/10 (2013.01); C02F 3/00 (2013.01); C07C 43/13 (2013.01); C12N 1/20 (2013.01); A62D 2101/28 (2013.01); C07D 319/10 (2013.01)

(58) Field of Classification Search
CPC ................................................... C07C 43/13
See application file for complete search history.

(56) References Cited

FOREIGN PATENT DOCUMENTS

| JP | 2008306939 A | 12/2008 |
|---|---|---|
| JP | 5877918 B1 | 3/2016 |
| JP | 2016077284 A | 5/2016 |

OTHER PUBLICATIONS

Adams et al., Oxidation and biodegradability enhancement of 1,4-dioxane using hydrogen peroxide and ozone, Environ. Sci. Technol., 1994, pp. 1812-1818, 28(11).
International Search Report (ISR) dated Jul. 12, 2016, issued for International application No. PCT/JP2016/062871.
Kohlweyer et al., Tetrahydrofuran degradation by a newly isolated culture of Pseudonocardia sp. strain K1, FEMS Microbiol. Lett., 2000, p. 301-306, vol. 186.
Kosaka et al., The effects of the co-existing compounds on the decomposition of micropollutants using the ozone/hydrogen peroxide process, Water Sci.Technol., 2000, pp. 353-361, vol. 42.
Mahendra et al., Kinetics of 1,4-dioxane biodegradation by monooxygenase-expressing bacteria, Environ. Sci. Technol., Jul. 25, 2006, pp. 5435-5442, 40(17).
Notification of Transmittal of Translation of the International Preliminary Report on Patentability (PCT/IB/338) dated Nov. 23, 2017, with International Preliminary Report on Patentability (PCT/IB/373) and Written Opinion of the International Searching Authority (PCT/ISA/237), for corresponding international application PCT/JP2016/062871.
Sales et al., Genome sequence of the 1,4-Dioxiane-degrading pseudonocardia dioxanivorans strain CB1190, J. Bacteriol., 2011, p. 4549-4550, vol. 193.
Sei et al., Challenge for biotreatment of groundwater contaminated with 1,4-dioxane by 1,4-dioxane-degrading bacteria, J. Water and Waste water, 2011, pp. 555-560, vol. 53, No. 7.
Sei et al., Isolation and characterization of bacterial strains that have high ability to degrade 1,4-dioxane as a sole carbon and energy source, Biodegradation, 2013, p. 665-674, vol. 24, No. 5.
Yamamoto et al., A Study of Biotreatment for Groundwater Contaminated with 1,4-Dioxane, Report of Taisei Technology Center, 2013, pp. 1-4, No. 46.
Extended European Search Report (EESR) dated Sep. 13, 2018, issued for European counterpart patent application No. EP16792527.0 (5 pages).
Yamamoto et al., Characterization of newly isolated Pseudonocardia sp. N23 with high 1,4-dioxane-degrading ability, Journal of Bioscience and Bioengineering, vol. 125, No. 5, May 2018, pp. 552-558.

*Primary Examiner* — Bin Shen
(74) *Attorney, Agent, or Firm* — Law Office of Katsuhiro Arai

(57) ABSTRACT

An object of the present invention is to provide a constitutive 1,4-dioxane-degrading bacteria offering excellent maximum relative rates of degradation of 1,4-dioxane. As a means for achieving the object, the present invention provides a constitutive 1,4-dioxane-degrading bacteria being strain N23 deposited as Accession No. NITE BP-02032.

7 Claims, 8 Drawing Sheets

Specification includes a Sequence Listing.

```
GACGAACGCTGGCGGCGTGCTTAACACATGCAAGTCGAGCGGTAAGGCCTT
TCGGGGTACACGAGCGGCGAACGGGTGAGTAACACGTGGGTGACCTGCCCT
CAGCTCTGGGATAAGCCTGGGAAACTGGGTCTAATACCGGATATGACCTCTCA
TCGCATGGTGGGTGGTGGAAAGTTTTTCGGCTGGGGATGGGCCCGCGGCCTA
TCAGCTTGTTGGTGGGGTGATGGCCTACCAAGGCGACGACGGGTAGCCGGC
CTGAGAGGGCGACCGGCCACACTGGGACTGAGACACGGCCCAGACTCCTAC
GGGAGGCAGCAGTGGGGAATATTGCGCAATGGGCGGAAGCCTGACGCAGCG
ACGCCGCGTGGGGGATGACGGCCTTCGGGTTGTAAACCTCTTTCGCCAGGGA
CGAAGCGCAAGTGACGGTACCTGGATAAGAAGCACCGGCCAACTACGTGCC
AGCAGCCGCGGTAATACGTAGGGTGCGAGCGTTGTCCGGAATTATTGGGCGT
AAAGAGCTCGTAGGCGGTCTGTCGCGTCGGTCGTGAAAACCTGCAGCTTAA
CTGTGGGCTTGCGGTCGATACGGGCATGACTGGAGTTCGGCAGGGGAGACT
GGAATTCCTGGTGTAGCGGTGAAATGCGCAGATATCAGGAGGAACACCGGTG
GCGAAGGCGGGTCTCTGGGCCGATACTGACGCTGAGGAGCGAAAGCGTGGG
GAGCGAACAGGATTAGATACCCTGGTAGTCCACGCCGTAAACGGTGGGTGCT
AGGTGTGGGGGCCATTCCACGGTCTCTGTGCCGCAGCTAACGCATTAAGCAC
CCCGCCTGGGGAGTACGGCCGCAAGGCTAAAACTCAAAGGAATTGACGGGG
GCCCGCACAAGCGGCGGAGCATGTGGATTAATTCGATGCAACGCGAAGAAC
CTTACCTGGGTTTGACATGCACCAGACATCCCTAGAGATAGGGCTTCCCTTGT
GGTTGGTGTGCAGGTGGTGCATGGCTGTCGTCAGCTCGTGTCGTGAGATGTT
GGGTTAAGTCCCGCAACGAGCGCAACCCTCGTTCCATGTTGCCAGCGCGTTA
TGGCGGGGACTCATGGGAGACTGCCGGGGTCAACTCGGAGGAAGGTGGGGA
TGACGTCAAGTCATCATGCCCCTTATGTCCAGGGCTTCACACATGCTACAATG
GCAAGTACAGAGGGCTGCGAGACCGCGAGGTGGAGCGAATCCCTTAAAGCT
TGTCTCAGTTCGGATCGGGGTCTGCAACTCGACCCCGTGAAGTTGGAGTCGC
TAGTAATCGCAGATCAGCAACGCTGCGGTGAATACGTTCCCGGGCCTTGTAC
ACACCGCCCGTCACGTCACGAAAGTTGGTAACACCCGAAGCCGACGGCCTA
ACCCGTGAGGGAGGGAGTTGTCGAAGGTGGGACTGGCGATTGGGACG
```

(a) Strain N23

(b) Strain CB1190

SEQUENCE LISTING

<160> NUMBER OF SEQ ID NOS: 3

<210> SEQ ID NO 1
<211> LENGTH: 1440
<212> TYPE: DNA
<213> ORGANISM: Pseudonocardia sp.N23

<400> SEQUENCE: 1

```
gacgaacgct ggcggcgtgc ttaacacatg caagtcgagc ggtaaggcct ttcggggtac      60
acgagcggcg aacgggtgag taacacgtgg gtgacctgcc ctcagctctg ggataagcct     120
```

```
gggaaactgg gtctaatacc ggatatgacc tctcatcgca tggtgggtgg tggaaagttt      180
ttcggctggg gatgggcccg cggcctatca gcttgttggt ggggtgatgg cctaccaagg      240
cgacgacggg tagccggcct gagagggcga ccggccacac tgggactgag acacggccca      300
gactcctacg ggaggcagca gtggggaata ttgcgcaatg ggcggaagcc tgacgcagcg      360
acgccgcgtg ggggatgacg gccttcgggt tgtaaacctc tttcgccagg gacgaagcgc      420
aagtgacggt acctggataa gaagcaccgg ccaactacgt gccagcagcc gcggtaatac      480
gtagggtgcg agcgttgtcc ggaattattg ggcgtaaaga gctcgtaggc ggtctgtcgc      540
gtcggtcgtg aaaacctgca gcttaactgt gggcttgcgg tcgatacggg catgactgga      600
gttcggcagg ggagactgga attcctggtg tagcggtgaa atgcgcagat atcaggagga      660 acaccgqtgg cgaaggcggg tctctgggcc gatactgacg ctgaggagcg aaagcgtggg      720
gagcgaacag gattagatac cctggtagtc cacgccgtaa acggtgggtg ctaggtgtgg      780
gggccattcc acgqtctctg tgccgcagct aacgcattaa gcaccccgcc tggggagtac      840
ggccgcaagg ctaaaactca aaggaattga cgggggcccg cacaagcggc ggagcatgtg      900
gattaattcg atgcaacgcg aagaacctta cctgggtttg acatgcacca gacatcccta      960
gagatagggc ttcccttgtg gttggtgtgc aggtggtgca tggctgtcgt cagctcgtgt      1020
cgtgagatgt tgggttaagt cccgcaacga gcgcaaccct cgttccatgt tgccagcgcg      1080
ttatggcggg gactcatggg agactgccgg ggtcaactcg gaggaaggtg gggatgacgt      1140
caagtcatca tgccccttat gtccagggct tcacacatgc tacaatggca agtacagagg      1200
gctgcgagac cgcgaggtgg agcgaatccc ttaaagcttg tctcagttcg gatcggggtc      1260
tgcaactcga ccccgtgaag ttggagtcgc tagtaatcgc agatcagcaa cgctgcggtg      1320
aatacgttcc cgggccttgt acacaccgcc cgtcacgtca cgaaagttgg taacacccga      1380
agccgacggc ctaacccgtg agggagggag ttgtcgaagg tgggactggc gattgggacg      1440
```

<210> SEQ ID NO 2
<211> LENGTH: 20
<212> TYPE: DNA
<213> ORGANISM: Artificial Sequence
<220> FEATURE:
<223> OTHER INFORMATION: A universal primer "8F" for the 16S rRNA gene

<400> SEQUENCE: 2
agagtttgat cctggctcag                                                  20

<210> SEQ ID NO 3
<211> LENGTH: 19
<212> TYPE: DNA
<213> ORGANISM: Artificial Sequence
<220> FEATURE:
<223> OTHER INFORMATION: A universal primer "U1492R" for the 16S rRNA
      gene

<400> SEQUENCE: 3
ggttaccttg ttacgactt                                                   19

CONSTITUTIVE 1,4-DIOXANE-DEGRADING BACTERIA

This application is the U.S. National Phase under 35 U.S.C. § 371 of International Application PCT/JP2016/062871, filed Apr. 25, 2016, which claims priority to Japanese Patent Application No. 2015-096577, filed May 11, 2015 and No. 2015-205643, filed Oct. 19, 2015. The International Application was published under PCT Article 21(2) in a language other than English.

TECHNICAL FIELD

The present invention relates to a constitutive 1,4-dioxane-degrading bacteria.

BACKGROUND ART 1,4-dioxane is a cyclic ether expressed by the following formula (1). 1,4-dioxane is excellent in compatibility with water or organic solvent and is usually used as a reaction solvent for organic synthesis.

[Chem. 1]

(1)

The manufacturing and import volume of 1,4-dioxane in Japan in 2010 was about 4500 t/year and it is presumed that 1,4-dioxane was released into the environment by about 300 t/year. 1,4-dioxane is water-soluble, and thus 1,4-dioxane diffuses over a wide area when it is released into a water environment. Also, 1,4-dioxane is inferior in volatility, adsorption to solids, photodegradability, hydrolyzability, and biodegradability, and thus it is difficult to be removed from water. Since 1,4-dioxane has acute toxicity and chronic toxicity, and further, carcinogenicity is indicated, the contamination of water environments by 1,4-dioxane is considered to adversely affect humans and animals and plants. Therefore, in Japan, 1,4-dioxane is regulated by a tap water quality standard (0.05 mg/L or less), an environmental standard (0.05 mg/L or less), and a wastewater standard (0.5 mg/L or less).

Also, Non-Patent Literature 1 reports that industrial effluent containing 1,4-dioxane contains 1,3-dioxolane, 2-methyl-1,3-dioxolane, and other cyclic ethers in addition to 1,4-dioxane. In particular, 1,3-dioxolane has been confirmed to have toxic properties such as acute toxicity, which means that contaminated water, etc., containing 1,3-dioxolane must be treated properly.

The activated sludge method, active carbon adsorption method, and other conventional water treatment methods cannot fully remove 1,4-dioxane and other cyclic ethers from water. For example, only the advanced oxidation processes, each of which combines multiple physiochemical oxidation methods including ozone treatment with hydrogen peroxide added (O3/H2O2), ozone treatment under ultraviolet irradiation (O3/UV), and ozone treatment under radiation exposure or ultrasonic irradiation, have been confirmed to be effective in treating 1,4-dioxane. However, such advanced oxidation processes have not been used widely due to high initial and running costs. In addition, Non-Patent Literature 2 reports that the efficiency of treating 1,4-dioxane using any advanced oxidation processes would drop if an organic matter other than 1,4-dioxane is present.

In response to the need for a method to treat water containing 1,4-dioxane and other cyclic ethers at low cost and in a stable manner, Patent Literature 1 and Non-Patent Literature 3 each propose a 1,4-dioxane treatment using 1,4-dioxane-degrading bacteria. 1,4-dioxane-degrading bacteria are largely classified into two groups: bacteria that decompose 1,4-dioxane as a single carbon source (assimilative bacteria), and bacteria that can decompose 1,4-dioxane in the presence of tetrahydrofuran or other specific matrix (co-metabolic bacteria). In light of the above, it is more efficient, when treating 1,4-dioxane contained in underground water, effluent, etc., using 1,4-dioxane-degrading bacteria, to use assimilative bacteria because there is no need to add any specific matrix.

Assimilative bacteria are further classified into inducible type and constitutive type depending on whether or not a 1,4-dioxane-degrading enzyme is induced. As described in Non-Patent Literature 4, inductive 1,4-dioxane-degrading bacteria produce and secrete a degrading enzyme when an inducing substance, or 1,4-dioxane in this case, is present, which means that such bacteria must be acclimated before they can be used to treat 1,4-dioxane. On the other hand, constitutive 1,4-dioxane-degrading bacteria can be used to treat 1,4-dioxane right away, without being acclimated first, because they are continuously producing a degrading enzyme.

As described in Non-Patent Literature 3, however, constitutive 1,4-dioxane-degrading bacteria present a problem in that their maximum relative rates of degradation of 1,4-dioxane are lower than the maximum relative rates of degradation of 1,4-dioxane achieved using inductive 1,4-dioxane-degrading bacteria. In addition, it is not known whether or not the 1,4-dioxane-degrading bacteria disclosed in Patent Literature 1 and Non-Patent Literatures 3 and 4 are capable of degrading other cyclic ethers in the presence of 1,4-dioxane.

Patent Literature 2 filed by the inventors of the present application for patent proposes a method for culturing 1,4-dioxane-degrading bacteria, whereby 1,4-dioxane-degrading bacteria are grown using a medium that contains diethylene glycol. Since 1,4-dioxane-degrading bacteria exhibit an excellent capability to utilize diethylene glycol as a carbon source, they can be grown preferentially by using a medium that contains diethylene glycol, without applying sterilization treatment, even in a condition where other microorganisms are present.

BACKGROUND ART LITERATURE

Patent Literature

Patent Literature 1: Japanese Unexamined Patent Application Publication No. 2008-306939
Patent Literature 2: Japanese Patent No. 5877918

Non-Patent Literature

Non-patent Literature 1: CD. Adams, P A. Scaclan and N D. Secrist: Oxidation and biodegradability enhancement of 1,4-dioxane using hydrogen peroxide and ozone, Environ. Sci. Technol., 28(11), pp. 1812-1818, 1994.
Non-patent Literature 2: K. KOSAKA, H. YAMADA, S. MATSUI, and K. SHISHIDA: The effects of the co-existing compounds on the decomposition of micropollutants using the ozone/hydrogen peroxide process. Water Sci. Technol., 42, pp. 353-361, 2000.

Non-Patent Literature 3: KAZUNARI SEI, MICHIHIKO IKE: Challenge for biotreatment of groundwater contaminated with 1,4-dioxane by 1,4-dioxane-degrading bacteria, J. Water and Waste water, Vol. 53, No. 7, 2011.

Non-Patent Literature 4: K. Sei, K. Miyagaki, T. Kakinoki, K. Fukasako, D. Inoue and M. Ike: Isolation and characterization of bacterial strains that have high ability to degrade 1,4-dioxane as a sole carbon and energy source, Biodegradation, 24, 5, pp. 665-674, 2012.

SUMMARY OF THE INVENTION

Problems to Be Solved by the Invention

An object of the present invention is to provide a constitutive 1,4-dioxane-degrading bacteria offering excellent maximum relative rates of degradation of 1,4-dioxane.

Means for Solving the Problems

1. A constitutive 1,4-dioxane-degrading bacteria being strain N23 deposited as Accession No. NITE BP-02032.
2. A suspension containing a constitutive 1,4-dioxane-degrading bacteria according to 1.
3. A method for treating a cyclic ether in water, characterized by using a constitutive 1,4-dioxane-degrading bacteria according to 1 or a suspension according to 2.
4. A method for treating a cyclic ether in soil, characterized by using a constitutive 1,4-dioxane-degrading bacteria according to 1 or a suspension according to 2.
5. A method for treating a cyclic ether according to 3 or 4, characterized in that the cyclic ether is one or more types selected from 1,4-dioxane, 1,3-dioxolane, 2-methyl-1,3-dioxolane, and tetrahydrofuran.
6. A method for treating a cyclic ether according to any one of 3 to 5, characterized in that the method is performed in the presence of diethylene glycol.
7. A method for culturing a constitutive 1,4-dioxane-degrading bacteria being strain N23 deposited as Accession No. NITE BP-02032, characterized in that culturing is performed using a medium that contains one or more types selected from 1,4-dioxane, glyoxylic acid, glycolic acid, ethylene glycol, diethylene glycol, 1,4-butanediol, 1-butanol, tetrahydrofuran, glucose, and acetic acid.
8. A method for culturing a constitutive 1,4-dioxane-degrading bacteria being strain N23 deposited as Accession No. NITE BP-02032, characterized in that culturing is performed using a medium that contains one or more types selected from 1,4-dioxane, ethylene glycol, diethylene glycol, and 1,4-butanediol.

Effects of the Invention

Strain N23 is a constitutive 1,4-dioxane-degrading bacteria that continuously produces a degrading enzyme. As evident from its maximum relative rate of degradation of 1,4-dioxane, which is the highest among the constitutive degrading bacteria reported to date, strain N23 exhibits excellent dioxane degradation capability. Strain N23 can degrade 1,4-dioxane to an extremely low concentration of 0.017 mg/L or less, while being able to treat 1,4-dioxane present at a concentration as high as approx. 5200 mg/L. In addition to treating 1,4-dioxane, strain N23 also demonstrates an excellent capability to treat 1,3-dioxolane, 2-methyl-1,3-dioxolane, tetrahydrofuran, and other cyclic ethers, and can treat multiple cyclic ethers at the same time, as well.

Strain N23 can be used to treat cyclic ethers in water or soil. Because it is a constitutive 1,4-dioxane-degrading bacteria, strain N23 exhibits its high cyclic ether treatment capability right away, without being acclimated first, and therefore helps build a simple contamination treatment process offering high treatment capability. Strain N23 also has an excellent capability of utilizing diethylene glycol as a carbon source, which means that, in the presence of diethylene glycol, the amount of bacteria of strain N23 can be maintained at a high level even when other microorganisms are present. As a result, use of strain N23 to treat cyclic ethers in the presence of diethylene glycol allows for maintenance of a high level of cyclic ether treatment capability. Additionally, in the presence of diethylene glycol, such high level of cyclic ether treatment capability of strain N23 can be maintained in a stable manner even when the cyclic ether concentration fluctuates.

When a medium that contains diethylene glycol as a carbon source is used, strain N23 will grow preferentially even when microorganisms not having 1,4-dioxane degradation capability are present. By using a medium that contains diethylene glycol, strain N23 can be cultured easily and in large quantities, to enable supply of large quantities of bacteria required for treating water, soil, etc., that has been contaminated by cyclic ethers. Furthermore, since no sterilization facility or chemical is required, strain N23 can be cultured at very low cost.

Strain N23 has an excellent capability of utilizing 1,4-dioxane, glyoxylic acid, glycolic acid, ethylene glycol, diethylene glycol, 1,4-butanediol, 1-butanol, tetrahydrofuran, glucose, and acetic acid as carbon sources, so when a medium that contains one or more types of the foregoing is used, the rate of growth of strain N23 can be increased.

Furthermore, strain N23 has a superior capability of utilizing 1,4-dioxane, ethylene glycol, diethylene glycol, and 1,4-butanediol as carbon sources compared to microorganisms having no 1,4-dioxane degradation capability, which means that, by using a medium that contains, as a primary carbon source or sources, one or more types selected from 1,4-dioxane, ethylene glycol, diethylene glycol, and 1,4-butanediol, strain N23 can be cultured without having to sterilize other microorganisms.

BRIEF DESCRIPTION OF THE DRAWINGS

FIG. 6 Graphs showing how the 1,4-dioxane concentration changes over time in a system using strain N23 (a), and a system using strain CB1190 (b), in Example 4.

MODE FOR CARRYING OUT THE INVENTION

The present invention is explained in detail below.

1,4-dioxane-degrading bacteria are present in nature, and can be screened by culturing, in a medium that contains 1,4-dioxane as the only carbon source, a sample of sludge, etc., collected from water or soil contaminated by 1,4-dioxane. As mentioned above, 1,4-dioxane-degrading bacteria are largely classified into two types, which are assimilative bacteria and co-metabolic bacteria, and assimilative 1,4-dioxane-degrading bacteria are further classified into inducible type and constitutive type.

Figure 1:
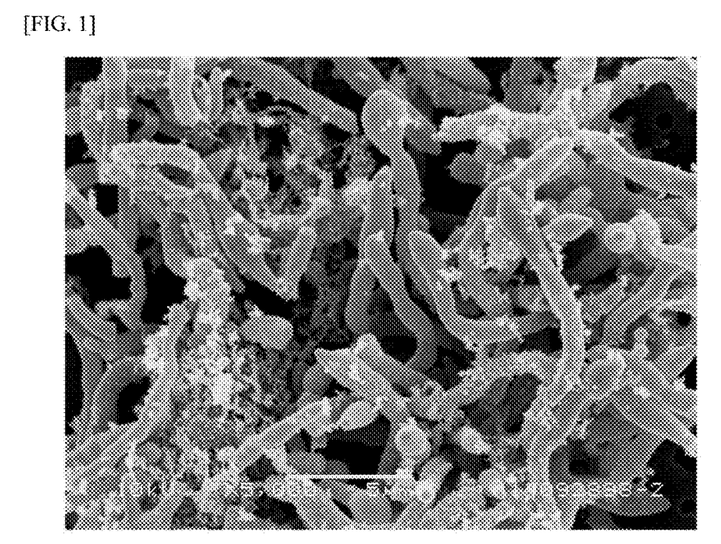
FIG. 1 SEM image of strain N23.

The constitutive 1,4-dioxane-degrading bacteria proposed by the present invention (hereinafter referred to as "strain N23") was isolated from underground water contaminated by 1,4-dioxane. Strain N23 was internationally deposited on Apr. 10, 2015 at the National Institute of Technology and Evaluation Patent Microorganisms Depository Center (NPMD) (2-5-8 Kazusakamatari, Kisarazu-shi, Chiba-ken, Japan (Postal Code 292-0818)), as Accession No. NITE BP-02032. A SEM image of strain N23 is shown in FIG. 1. Strain N23 is Gram-positive and catalase-positive.

Strain N23 is a constitutive 1,4-dioxane-degrading bacteria that continuously produces a degrading enzyme. In general, constitutive 1,4-dioxane-degrading bacteria exhibit lower maximum relative rates of degradation of 1,4-dioxane compared to inducible 1,4-dioxane-degrading bacteria; however, strain N23 exhibits the highest maximum relative rate of degradation of 1,4-dioxane among the constitutive 1,4-dioxane-degrading bacteria reported to date, and its value is equal to or higher than the maximum relative rates of degradation of 1,4-dioxane achieved by inducible 1,4-dioxane-degrading bacteria. In addition, strain N23 can decompose 1,4-dioxane to an extremely low concentration of 0.017 mg/L or less, while being able to treat 1,4-dioxane present at a concentration as high as approx. 5200 mg/L. Since strain N23 need not be acclimated using 1,4-dioxane, etc., achieves a high maximum relative rate of degradation of 1,4-dioxane, and is able to decompose 1,4-dioxane to an extremely low concentration and treat 1,4-dioxane present at a high concentration, it can be utilized favorably in the biological treatment of 1,4-dioxane.

In addition to 1,4-dioxane, strain N23 can also efficiently decompose 1,3-dioxolane, 2-methyl-1,3-dioxolane, tetrahydrofuran and other cyclic ethers. It can also treat multiple cyclic ethers at the same time. Accordingly, strain N23 can be utilized favorably in the biological treatment of 1,4-dioxane, 1,3-dioxolane, 2-methyl-1,3-dioxolane, tetrahydrofuran and other cyclic ethers.

Figure 2:
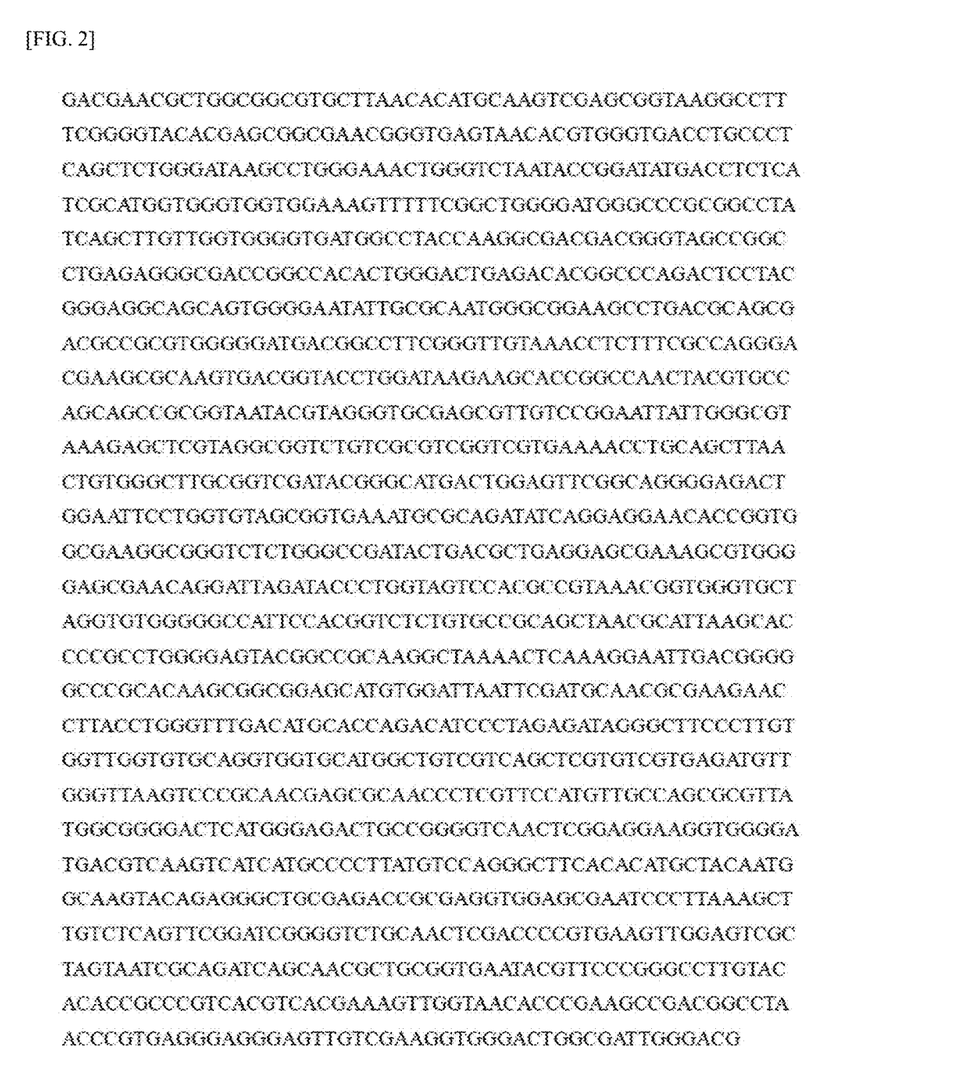
FIG. 2 Partial 16S rDNA base sequence of strain N23 (SEQ ID NO: 1).

The 16S rDNA of strain N23 was amplified by the PCR method using 8F (5'-AGAGTTTGATCCTGGCTCAG-3') (SEQ ID NO: 2) and U1492R (5'-GGTTACCTTGTTAC-GACTT-3') (SEQ ID NO: 3) as primers, and the obtained amplified product was put through sequence analysis. The partial 16S rDNA base sequence of strain N23 is shown in FIG. 2, and in the sequence listing under SEQ ID NO: 1.

Figure 3:
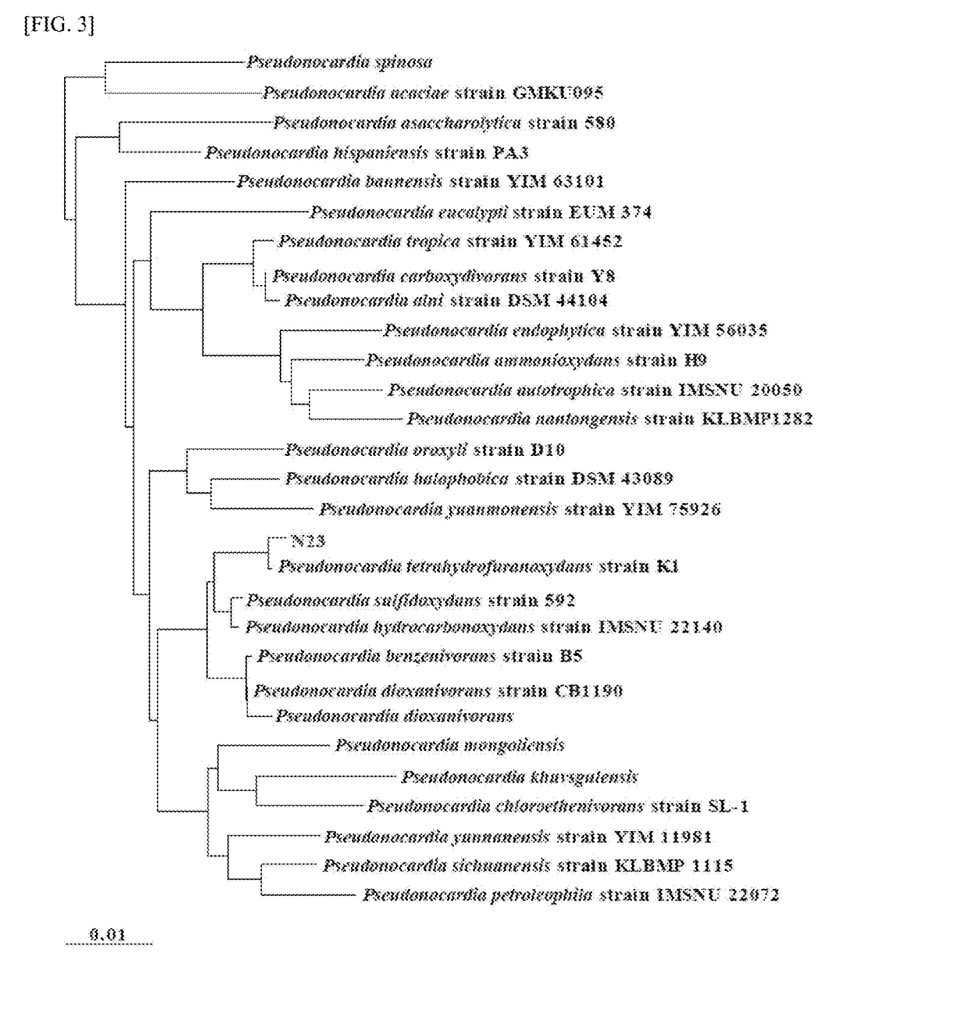
FIG. 3 Family tree diagram prepared based on the 16S rDNA base sequence of strain N23.

When homology search was performed on the partial 16S rDNA base sequence of strain N23 using the BLAST from DDBJ (DNA Data Bank of Japan), strain N23 showed high homology of 99% with Pseudonocardia tetrahydrofuranoxy-dans strain K1 (hereinafter referred to as "strain K1"). Here, strain K1 is a co-metabolizing bacteria that decomposes 1,4-dioxane by means of co-metabolization (S. Mahendra and L. Alvarez-Cohen: Kinetics of 1,4-dioxane biodegradation by monooxygenase-expressing bacteria, Environ. Sci. Technol., 40 (17), pp 5435-5442, 2006). In the meantime, strain N23 is an assimilative bacteria that decomposes 1,4-dioxane as a single carbon source. This means that, while it exhibits high homology of 99% with strain K1, strain N23 is clearly a different type of bacteria from strain K1. A family tree diagram created based on the 16S rDNA base sequence is shown in FIG. 3.

Examples of media used for culturing strain N23 include liquid medium and solid medium. Such media are not limited in any way so long as they can culture strain N23, and any known medium such as the MGY medium or CGY medium can be used. To culture a large quantity of strain N23, preferably a liquid medium is used, and more preferably continuous culturing is performed whereby, while a liquid medium is being supplied, a culture solution containing strain N23 is taken out by the same quantity as the supplied quantity of liquid medium.

Necessary inorganic matters and organic matters can be added when culturing strain N23. The amount of activity of microorganisms is limited by, among the necessary nutrients and all other factors affecting such amount of activity, the factor of the least quantity; accordingly, growth of strain N23 can be promoted by adding lacking nutrients. The inorganic matters to be added are not limited in any way, and include $K_2HPO_4$, $(NH_4)_2SO_4$, $MgSO_4 \cdot 7H_2O$, $FeCl_3$, $CaCl_2$, and NaCl, among others. Also, while the organic matters to be added are not limited in any way, corn steep liquor, casamino acid, yeast extract, peptone, etc., are preferred.

Strain N23 has an excellent capability of utilizing 1,4-dioxane, glyoxylic acid, glycolic acid, ethylene glycol, diethylene glycol, 1,4-butanediol, 1-butanol, tetrahydrofuran, glucose, and acetic acid, as carbon sources. The rate of growth of strain N23 can be increased by using a medium that contains one or more types selected from 1,4-dioxane, glyoxylic acid, glycolic acid, ethylene glycol, diethylene glycol, 1,4-butanediol, 1-butanol, tetrahydrofuran, glucose, and acetic acid. The total concentration of the aforementioned compound(s) in the medium is not limited in any way; however, preferably it is $1.0 \times 10^{-8}$ percent by weight or more but no more than 10.0 percent by weight. The lower limit of total concentration is more preferably 0.1 percent by weight or more, or even more preferably 0.5 percent by weight or more, or most preferably 1.0 percent by weight or more. The upper limit of total concentration is more preferably 9.0 percent by weight or less, or even more preferably 8.0 percent by weight or less, or most preferably 7.0 percent by weight or less. In addition, the total sum of the aforementioned compound(s) is preferably 60 percent by weight or more, or more preferably 80 percent by weight or more, or even more preferably 95 percent by weight or more, or most preferably 99.9 percent by weight or more, relative to the total quantity of organic compounds in the medium.

Furthermore, since strain N23 has a superior capability of utilizing 1,4-dioxane, ethylene glycol, diethylene glycol, and 1,4-butanediol as carbon sources, compared to microorganisms not having 1,4-dioxane degradation capability, it is more preferable that the medium contains, as a primary carbon source or sources, one or more types selected from 1,4-dioxane, ethylene glycol, diethylene glycol, and 1,4-butanediol. The total sum of 1,4-dioxane, ethylene glycol, diethylene glycol, and 1,4-butanediol is preferably 60 percent by weight or more, or more preferably 80 percent by weight or more, or even more preferably 95 percent by weight or more, or most preferably 99.9 percent by weight or more, relative to the total quantity of organic compounds in the medium.

Microorganisms not having 1,4-dioxane degradation capability are inferior to strain N23 in their capability of utilizing 1,4-dioxane, ethylene glycol, diethylene glycol, and 1,4-butanediol as carbon sources, which means that, if a medium containing any of the foregoing is used to culture strain N23 and a microorganism not having 1,4-dioxane degradation capability, strain N23 will grow preferentially. This means that strain N23 can be cultured without applying sterilization treatment beforehand, by using a medium that contains, as a primary carbon source or sources, one or more types selected from 1,4-dioxane, ethylene glycol, diethylene glycol, and 1,4-butanediol. Culturing methods that require sterilization present difficulty in terms of sterilizing the equipment in every part thereof, which in turn makes it difficult to perform culturing using large-capacity equipment.

In contrast, no sterilization treatment is required when strain N23 is cultured using a medium that contains, as a primary carbon source or sources, one or more types selected from 1,4-dioxane, ethylene glycol, diethylene glycol, and 1,4-butanediol, which means that large-scale culturing is possible and large quantities of bacteria needed to treat water, soil, etc., that has been contaminated by cyclic ethers can be supplied. Strain N23 can be cultured easily using a medium that contains, as a primary carbon source or sources, one or more types selected from 1,4-dioxane, ethylene glycol, diethylene glycol, and 1,4-butanediol, because contamination by other microorganisms does not occur. In addition, there is no need for sterilization facility or chemicals, which allows for culturing at very low cost.

Strain N23 proposed by the present invention can be used to treat cyclic ethers contained in plant effluent, sewage water, groundwater, or other contaminated water, or in contaminated soil at industrial waste treatment facilities, factories, illegal dumping sites, or the like. Strain N23 is a constitutive 1,4-dioxane-degrading bacteria that continuously produces a degradation enzyme, and therefore cyclic ether treatment can be started right away. Strain N23 can be used to treat cyclic ethers in any desired form, such as bacterial cells that have been filtered out from a culture solution, bacterial cells that have been frozen and stored, bacterial cells that have been L-dried and stored, bacterial cells that have been freeze-dried, an immobilization carrier comprising strain N23 that has been fixed on a resin, etc., or a suspension that contains strain N23 in the form of culture solution or concentrate thereof. Since cyclic ethers can be treated simply by causing strain N23 to come in contact with the treatment target that has been contaminated by the cyclic ethers, a contamination treatment process which is simple yet demonstrates high treatment capability can be developed.

Strain N23 can be used to treat cyclic ethers in contaminated water. The method for treating cyclic ethers in contaminated water using strain N23 is not limited in any way and, in the case of treating contaminated water according to the conventional activated sludge method using an aeration tank, for example, the cyclic ethers in contaminated water can be treated by simply adding strain N23 to the aeration tank in the form of an immobilization carrier, suspension, etc. Since adding strain N23 to the aeration tank is all that is required to biologically treat the cyclic ethers, any facility which would be used under the conventional standard activated sludge method can be utilized virtually as is. In addition, strain N23 can be easily cultured using any commercially available equipment as long as a medium that contains diethylene glycol is used, which means that, at the contaminated water treatment site, a culture solution containing strain N23 can be continuously introduced to contaminated water through the continuous culturing mentioned above.

Diethylene glycol may be added to the contaminated water to be treated with strain N23. In this case, preferably diethylene glycol is introduced in such a way that the concentration of diethylene glycol in the contaminated water becomes $1.0 \times 10^{-8}$ percent by weight or more but no more than 10.0 percent by weight. The lower limit of diethylene glycol concentration is more preferably 0.1 percent by weight or more, or even more preferably 0.5 percent by weight or more, or most preferably 1.0 percent by weight or more. The upper limit of diethylene glycol concentration is more preferably 6.0 percent by weight or less, or even more preferably 3.0 percent by weight or less, or most preferably 2.0 percent by weight or less. Although various types of microorganisms are present in any contaminated water to be biologically treated, the percentage of the amount of bacterial cells of strain N23 to the total amount of bacterial cells in the contaminated water can be maintained at a high level, and therefore the cyclic ether treatment capability can be kept at a high level, by adding diethylene glycol to the contaminated water. Also, in the contaminated water where the cyclic ether concentration fluctuates, the amount of bacterial cells of strain N23 decreases when the cyclic ether concentration drops, and therefore the amount of bacterial cells of strain N23 may become insufficient when the cyclic ether concentration rises later, and the cyclic ethers in the contaminated water may not be treated fully as a result. By adding diethylene glycol to the contaminated water, the cyclic ether treatment capability can be kept at a high level in a stable manner even when the cyclic ether concentration fluctuates. It should be noted that diethylene glycol has little adverse effect on the environment.

Cyclic ethers in contaminated soil can be treated using strain N23. In this case, preferably diethylene glycol is added in such a way that the concentration of diethylene glycol in contaminated soil becomes 0.1 percent by weight or more but no more than 10 percent by weight. The lower limit of diethylene glycol concentration is more preferably 0.5 percent by weight or more, or even more preferably 1 percent by weight or more, or most preferably 2 percent by weight or more. The upper limit of diethylene glycol concentration is more preferably 8 percent by weight or less, or even more preferably 7 percent by weight or less, or most preferably 5 percent by weight or less. The method for treating cyclic ethers in contaminated soil using strain N23 is not limited in any way, and a method in which strain N23 is added to the contaminated soil and the two may be mixed and agitated, a method in which a suspension containing strain N23 is injected into the contaminated soil, or the like may be used. However, injecting a suspension containing strain N23 into the soil is preferred, because there is no need for constructing a plant, digging, detoxifying, or backfilling the soil or implementing any other process at the site. Preferably carbon sources, inorganic salts, etc., are injected, or more preferably diethyl glycol is injected as a carbon source, into the contaminated soil because such soil generally lacks nutrients. By adding diethylene glycol to the soil, cyclic ethers in the soil can be treated more quickly.

EXAMPLES

Example 1

[Determination of Partial 16S rDNA Base Sequence of Strain N23]

Strain N23 was cultured for seven days using a CGY liquid medium (5 g/L of Casitone, 5 g/L of glycerin, 1 g/L of yeast extract) (28° C., 120 rpm). The culture solution was centrifuged for 3 minutes at 10000×g at 4° C., after which the bacteria were collected and washed twice with 0.9% saline solution. From the cleaned bacterial cells thus obtained, DNA was extracted according to "Current Protocols in Molecular Biology I, Preparation of Genomic DNA from Bacteria, Basic Protocol 1: Miniprep of Bacterial Genomic DNA" (translated by Kaoru Saigo and Yumiko Sano, pp. 36-37, Maruzen Corporation, 1997), and 16S rDNA was amplified according to the PCR method. 8F (5'-AGAGTTTGATCCTGGCTCAG-3') (SEQ ID NO: 2) and U1492R (5'-GGTTACCTTGTTACGACTT-3') (SEQ ID NO: 3) were used as primers. The PCR amplification involved repeating the cycle of holding for 10 minutes at 94° C., denaturing (for 1 minute at 94° C.), annealing (for 1 minute at 58° C.), and stretching (for 2 minutes at 72° C.) the sample for 35 cycles, and finally holding the sample for 10 minutes at 72° C.

The amplified product thus obtained was moved electrophoretically using 2% agarose gel. Thereafter, the target band was cut out and refined using the MinElute Gel Extraction Kit (QUIAGEN), and the obtained amplified product was put through sequence analysis. The partial 16S rDNA base sequence of strain N23 is shown in FIG. 2 (SEQ ID NO: 1).

Homology search was performed on the obtained partial 16S rDNA base sequence using the BLAST from DDBJ. As a result, strain N23 exhibited high homology with Pseudonocardia tetrahydrofuranoxydans strain K1 (strain K1), and its value was 99%.

Example 2

[Study of 1,4-Dioxane Degradation Characteristics of Strain N23]

100 mL of CGY medium (5 g/L of Casitone, 5 g/L of glycerin, 1 g/L of yeast extract) was added to a baffled triangle flask with a capacity of 300 mL, and sterilized in an autoclave (for 15 minutes at 121° C.). Thereafter, 1,4-dioxane was added so as to be a total of 500 mg/L, and then one platinum loop full of strain N23 was inoculated and cultured under rotary shaking for seven days (at 28° C., 120 rpm) (pre-advance culturing).

After the culturing, the sample was subcultured onto a CGY medium containing 500 mg/L of 1,4-dioxane, and cultured under the same conditions (advance culturing).

The culture solution obtained from the advance culturing was centrifuged to collect and recover the bacteria, which were then washed by adding an inorganic salt medium (composition: 1 g/L of $K_2HPO_4$, 1 g/L of $(NH_4)_2SO_4$, 50 mg/L of NaCl, 200 mg/L of $MgSO_4 \cdot 7H_2O$, 10 mg/L of $FeCl_3$, 50 mg/L of $CaCl_2$, pH: 7.3).

The inorganic salt medium in which the bacterial cells were suspended was used as an inoculum suspension.

The inoculum suspension was added to 100 mL of inorganic salt medium, after which 1,4-dioxane was added so as to be a total of 1.25 mg/L and cultured under rotary shaking at 28° C. and 120 rpm (n=3). It should be noted that the concentration of protein in the inoculum suspension was measured beforehand according to the method reported by P R. Meyers et al. (P R. Meyers, W R. Bourn, L M. Steyn, P D. van Helden, A D. Beyers, and G D. Brown: Novel method for rapid measurement of growth of mycobacteria in detergent-free medium, J Clin Microbiol., 36 (9), pp. 2752-2754, 1998), and the solution was prepared to achieve a protein concentration of 30 mg/L at the start of test. Culturing was performed for 12 hours, and the concentration of 1,4-dioxane in the solution was measured every two hours using a head space gas chromatograph mass spectrometer (GC/MS-QP2010 PLUS TURBOMATRIX HS40 manufactured by Shimadzu Corporation, hereinafter referred to as "head space GC/MC"). An experimental system to which strain N23 was not added was also measured for comparison.

Figure 4:
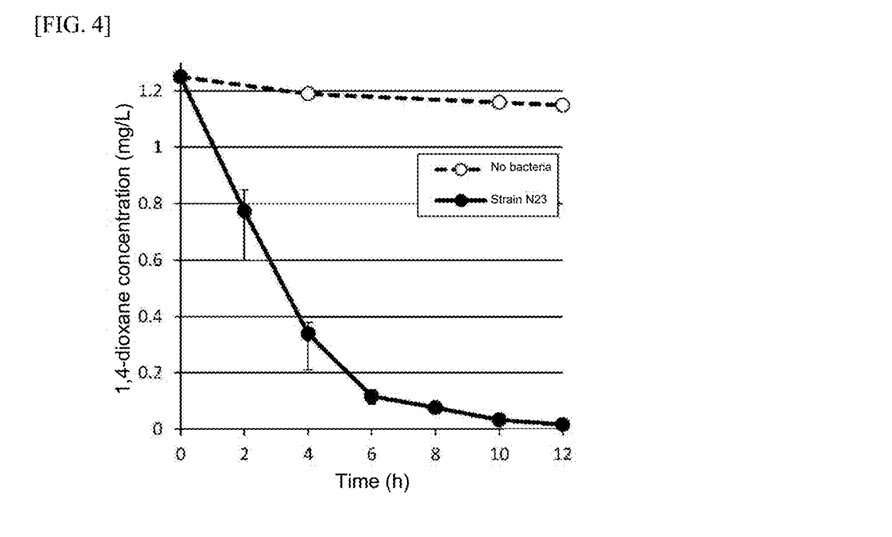
FIG. 4 Graph showing how the 1,4-dioxane concentration changes over time in Example 2.

FIG. 4 shows how the 1,4-dioxane concentration changed over time. With the experimental system to which strain N23 was added, the 1,4-dioxane concentration dropped over time, reaching 0.033 mg/L after 10 hours of culturing and 0.017 mg/L after 12 hours of culturing. With the experimental system to which strain N23 was not added, on the other hand, the 1,4-dioxane concentration hardly dropped and the concentration remained 1.15 mg/L after 12 hours of culturing. This confirms that strain N23 is a 1,4-dioxane-degrading bacteria capable of decomposing 1,4-dioxane to an extremely low concentration range.

Example 3

[Confirmation of Growth Property of Strain N23 Due to 1,4-Dioxane]

Figure 5:
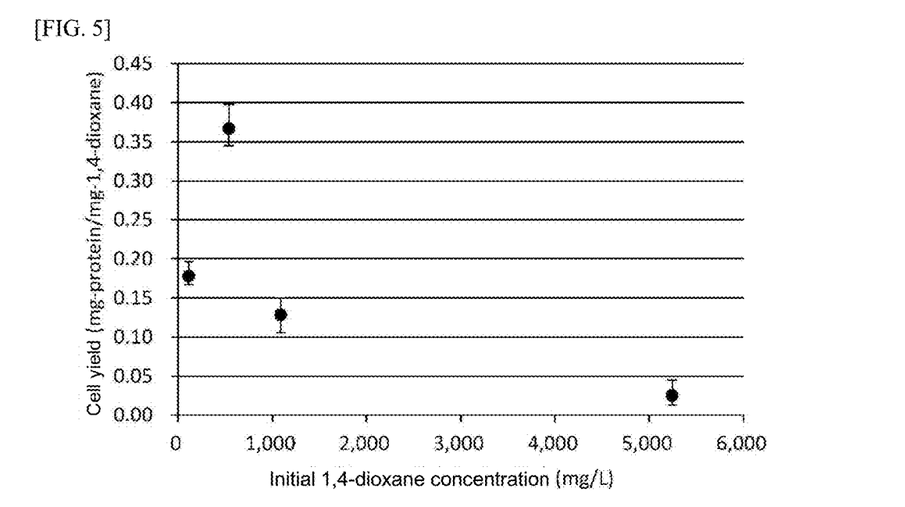
FIG. 5 Graph showing the relationship between the initial 1,4-dioxane concentration, and the cell yield, in Example 3.

After adding 1 mL of the strain N23 inoculum suspension prepared in Example 2, to 19 mL of inorganic salt medium, 1,4-dioxane was added to a specified concentration and the sample was cultured under rotary shaking at 28° C. and 120 rpm (n=3). Culturing was performed for six hours, and before and after the culturing, the 1,4-dioxane concentration was measured using the head space GC/MS, and the protein concentration was also measured according to the method described in Example 2. The rate of increase in protein mass with respect to 1,4-dioxane degradation quantity was calculated as the cell yield. FIG. 5 shows the relationship between the initial 1,4-dioxane concentration and the cell yield.

In all experimental systems, the mass of protein increased, which confirms that strain N23 grew using 1,4-dioxane as a carbon source. In particular, the experimental system whose initial 1,4-dioxane concentration as approx. 540 mg/L showed excellent growth property of 0.37 mg-protein/mg-1,4-dioxane. Also, the experimental system whose initial 1,4-dioxane concentration was approx. 5200 mg/L showed a cell yield value of 0.025 mg-protein/mg-1,4-dioxane, confirming that strain N23 grew even under a condition of high 1,4-dioxane concentration. In other words, strain N23 is clearly capable of treating contaminated water containing a high concentration of 1,4-dioxane.

The above results show that strain N23 is an assimilation bacteria that can grow using 1,4-dioxane as a single carbon source. Strain N23 was estimated as a bacteria similar to Pseudonocardia tetrahydrofuranoxydans strain K1 based on the result of Example 1. However, now it is shown that strain N23 is an assimilation bacteria and strain K1 is a co-metabolizing bacteria; strain N23 and strain K1 are different bacteria.

Example 4

[Study of Property of Strain N23 to Induce 1,4-Dioxane-Degrading Enzyme]

Degradation test was performed using inoculum suspensions, prepared using a system to which 1,4-dioxane was added (inducible system) and not added (non-inducible system) in the advance culturing described in Example 2, respectively. For the 1,4-dioxane-degrading bacteria, strain N23, and Pseudonocardia dioxanivorans CB1190 (hereinafter referred to as "strain CB1190") which is a known inducible 1,4-dioxane-degrading bacteria, were used. It should be noted that strain CB1190 was purchased from ATCC in the U.S. (ATCC 55486).

Figure 6:
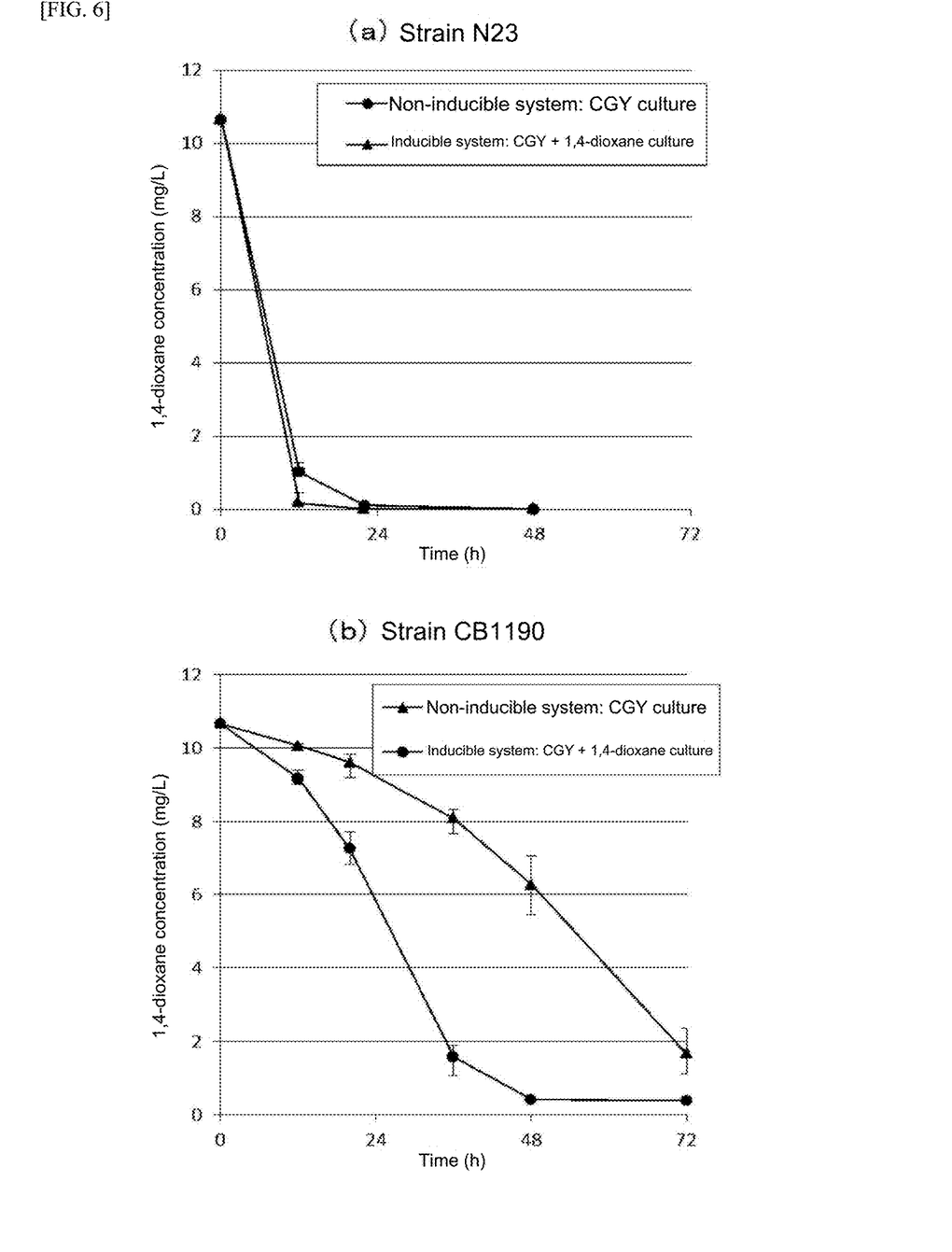

Each inoculum suspension was prepared according to the method described in Example 2, in such a way that the protein concentration would become 10 mg/L at the start of test. After adding 1 mL of inoculum suspension to 19 mL of inorganic salt medium, 1,4-dioxane was added to a specified concentration (n=3). During the period of experimentation, the 1,4-dioxane concentration was measured using the head space GC/MS by performing sampling as deemed appropriate. FIG. 6 (a) shows how the 1,4-dioxane concentration changes over time in the system using strain N23, while FIG. 6(b) shows the same in the system using strain CB1190.

As shown in FIG. 6(b), the system in which strain CB1190 was cultured in a CGY medium to which 1,4-dioxane was not added (non-inducible system) showed a gradual drop in 1,4-dioxane concentration. In the system in which the strain was cultured by adding 1,4-dioxane (inducible system), on the other hand, the 1,4-dioxane concentration was lower, confirming that the rate of degradation was higher, compared to the non-inducible system. This difference in the rate of degradation is probably due to whether or not a degrading enzyme was induced by 1,4-dioxane in the advance culturing, which confirms that the 1,4-dioxane-degrading enzyme of strain CB1190 is an inducible enzyme. The degrading enzyme inducibility property of strain CB1190 is also reported by Kelley et al. (S L. Kelley, E W. Aitchison, M. Deshpande, J L. Schnoor, P J. Alvarez: Biodegradation of 1,4-dioxane in planted and unplanted soil: effect of bioaugmentation with Amycolatasp. CB1190, Water Res., 35 (16), pp. 3791-800, 2001).

With strain N23, on the other hand, no marked difference was confirmed between the 1,4-dioxane concentration change in the non-inducible system and that in the inducible system, as shown in FIG. 6(a). Similar results are reported in the aforementioned Non-Patent Literature 4, and since bacteria showing such behaviors are classified as constitutive, strain N23 is confirmed to be a constitutive 1,4-dioxane-degrading bacteria. Also, strain N23 was superior to the inducible strain CB1190 in its 1,4-dioxane degradation capability.

Example 5

[Measurement of Maximum Relative Rate of Degradation of 1,4-Dioxane by Strain N23]

Degradation test was performed using the inoculum suspensions prepared according to the procedure in Example 2. After adding 1 mL of inoculum suspension to 19 mL of inorganic salt medium, 1,4-dioxane was added to a specified concentration and the sample was cultured for eight hours under rotary shaking at 28° C. and 120 rpm. The experiment was performed on two samples (n=2) per each of the systems whose initial 1,4-dioxane concentration was adjusted to 11, 107, 258, 564 and 1136 mg/L, respectively. During the period of experimentation, sampling was performed every hour or two hours, and the 1,4-dioxane concentration was measured using the head space GC/MS. How the 1,4-dioxane concentration changed over time was expressed in a graph using the averages of measured values, and for each system, the slope (1,4-dioxane degradation quantity per hour) was divided by the protein mass at the start of experimentation, to obtain the relative rate of degradation. It should be noted that the relative rate of degradation was calculated by measuring an experimental system to which strain N23 was not added, and subtracting the decrease in 1,4-dioxane due to volatilization. According to the method described in Example 2, the initial protein concentration was set to a range of 128 to 206 mg/L. Measurement was performed in the same manner for strain CB1190.

Figure 7:
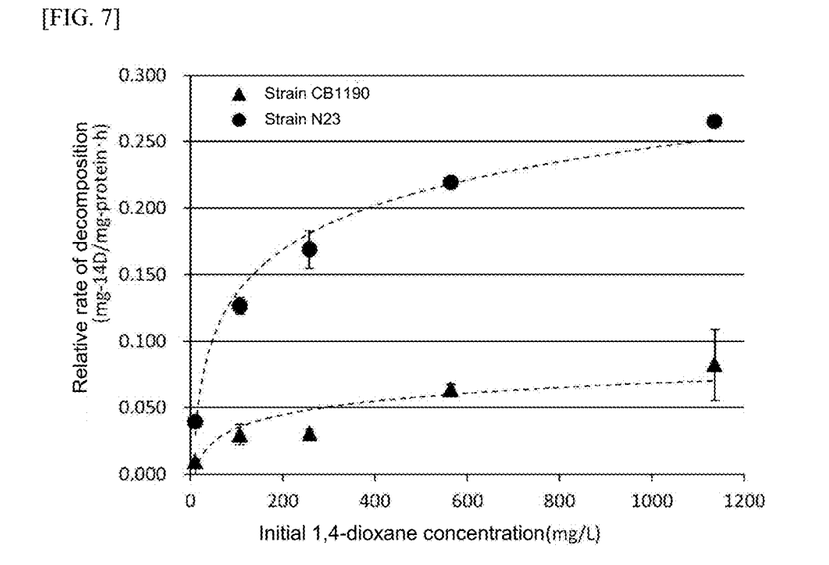
FIG. 7 Graph showing the relative rate of degradation, with respect to the initial 1,4-dioxane concentration, in Example 5.

FIG. 7 shows the relative rate of degradation with respect to the initial 1,4-dioxane concentration.

It is clear that the relationship follows the typical Monod equation in that, when the matrix is low in concentration, the relative rate of degradation increases proportionally with the concentration; once the matrix concentration increases to a certain level, however, it plateaus and becomes gradually closer to the maximum relative rate of degradation. When the maximum relative rate of degradation was obtained for each strain based on this analysis result, it was 0.051 mg-1,4-dioxane/mg-protein·h with strain CB1190. With strain N23, on the other hand, the maximum relative rate of degradation was 0.216 mg-1,4-dioxane/mg-protein·h, which is roughly 4.2 times the value with strain CB1190. Also, in the aforementioned Non-Patent Literature 3, Sei et al. conducted a study of the maximum relative rates of degradation of 1,4-dioxane-degrading bacteria. Table 1 shows the result of Example 5, as well as the strains, their types, and maximum relative rates of degradation achieved by the strains, as described in the aforementioned Non-Patent Literature 3. Strain N23 demonstrates a maximum relative rate of degradation 2.3 to 4.2 times as high as the rates achieved by the constitutive 1,4-dioxane-degrading bacteria reported to date. Also, this value is equivalent to or higher than the rates achieved by the inducible 1,4-dioxane-degrading bacteria. This confirms that strain N23 is a bacterial strain achieving a high maximum relative rate of degradation of 1,4-dioxane, compared to the constitutive 1,4-dioxane-degrading bacteria reported to date.

TABLE 1

| Bacterial strain | | Maximum relative rate of degradation of 1,4-dioxane (mg-1,4-dioxane/mg-protein · h) |
|---|---|---|
| Strain N23 | Constitutive | 0.216 |
| Strain CB1190 | Inducible | 0.051 |
| *Afipia* sp. Strain D1 | Inducible | 0.263 |
| *Mycobacterium* sp. Strain D6 | Inducible | 0.139 |
| *Mycobacterium* sp. Strain D11 | Constitutive | 0.052 |
| *Pseudonocardia* sp. Strain D17 | Constitutive | 0.096 |

Example 6

[Study of Degradation 1,3-Dioxolane and 2-Methyl-1,3-Dioxolane Using Strain N23]

Experimentation was conducted to check if strain N23, which is a constitutive 1,4-dioxane-degrading bacteria, is capable of degrading 1,3-dioxolane and 2-methyl-1,3-dioxolane. In the degradation test, 1 mL of inoculum suspension was added to 19 mL of inorganic salt medium, after which three types of cyclic ethers, namely, 1,4-dioxane, 1,3-dioxolane and 2-methyl-1,3-dioxolane, were added (n=3) to a specified concentration. During the period of experiment, the concentrations of 1,4-dioxane, 1,3-dioxolane and 2-methyl-1,3-dioxolane were measured using the head space GC/MS by performing sampling as deemed appropriate. It should be noted that the inoculum suspension was prepared beforehand according to the method described in Example 2, so that the protein concentration would be approx. 90 mg/L at the start of test.

Figure 8:
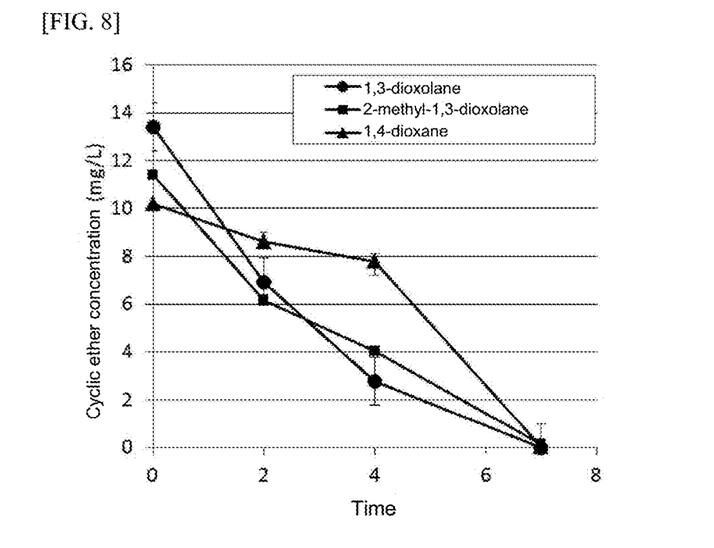
FIG. 8 Graph showing how the cyclic ether concentration changes over time in Example 6.

FIG. 8 shows how the concentration of each cyclic ether changed over time. It was confirmed that the concentrations of all cyclic ethers dropped immediately after the start of experiment. In other words, this confirms that strain N23 can degrade 1,4-dioxane, 1,3-dioxolane and 2-methyl-1,3-dioxolane simultaneously and that it can be utilized in the treatment of multiple types of cyclic ethers.

Example 7

[Confirmation of Growth Property of Strain N23 by Different Carbon Source]

Strain N23 was cultured for seven days using a CGY liquid medium (5 g/L of Casitone, 5 g/L of glycerin, 1 g/L of yeast extract) (28° C., 120 rpm). The culture solution was centrifuged for 3 minutes at 10000×g and 4° C., after which the bacteria were collected and washed twice with 0.9% saline solution. Thereafter, 0.9% saline solution was used to suspend the bacteria to a specified concentration, to prepare an inoculum suspension.

Figure 9:
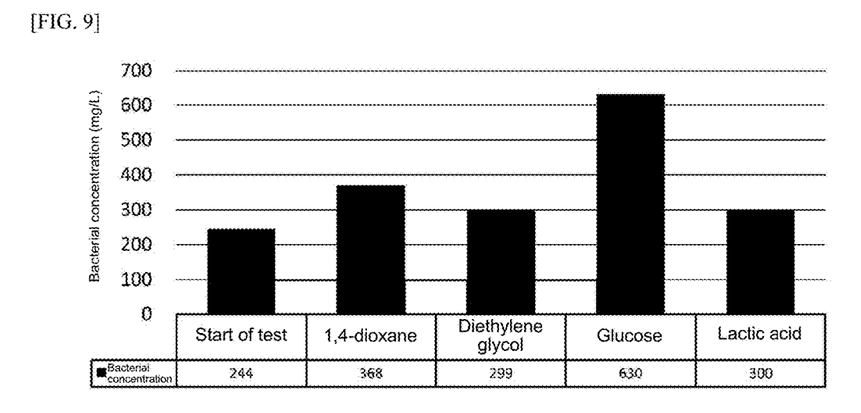
FIG. 9 Graph showing the bacterial cell concentrations at the end of culturing, by carbon source, in Example 7.

100 mL of inorganic salt medium (composition: 1 g/L of $K_2HPO_4$, 1 g/L of $(NH_4)_2SO_4$, 50 mg/L of NaCl, 200 mg/L of $MgSO_4.7H_2O$, 10 mg/L of $FeCl_3$, 50 mg/L of $CaCl_2$, pH: 7.3) was added to a baffled triangle flask with a capacity of 300 mL, and autoclaved for 15 minutes at 121° C. Thereafter, a carbon source was added to 1 g/L, and then the strain N23 inoculum suspension was added (initial bacterial cell concentration: 244 mg-dry/L) and the sample was cultured under rotary shaking at 28° C., and 120 rpm (n=2). It should be noted that, for the carbon source, 1,4-dioxane, diethylene glycol, glucose, and lactic acid were used, respectively. The culturing ended on the fourth day after the start of test, upon which the bacterial cells in the solution were recovered, as a filter residue, by means of suction filtration, and then dried overnight at 105° C., after which the weight of bacterial cells was measured to obtain the bacterial cell concentration (mg/L) at the end of culturing. FIG. 9 shows the bacterial cell concentration at the end of culturing, by each carbon source.

Growth of strain N23 was confirmed with all carbon sources, and particularly in the system cultured with glucose, the bacterial cell concentration was the highest after four days of culturing. In an environment where other microorganisms are present, however, it is difficult to preferentially grow strain N23 using glucose as a carbon source, because glucose can also be utilized by other microorganisms as their growth matrix. On the other hand, diethylene glycol can specifically grow 1,4-dioxane-degrading bacteria, as reported in the aforementioned Patent Literature 2. Since strain N23 can utilize diethylene glycol as a carbon source, strain N23 can be grown preferentially to other microorganisms using diethylene glycol.

Example 8

[Confirmation of Growth Property of Strain N23 by Different Carbon Source 2]

Strain N23 was cultured for two weeks using a MGY medium (10 g/L of malt extract, 4 g/L of glucose, 4 g/L of yeast extract, pH: 7.3). The culture solution was centrifuged for 3 minutes at 10000×g and 4° C., after which the bacteria were collected and washed twice with an inorganic salt medium (composition: 1 g/L of $K_2HPO_4$, 1 g/L of $(NH_4)_2SO_4$, 50 mg/L of NaCl, 200 mg/L of $MgSO_4.7H_2O$, 10 mg/L of $FeCl_3$, 50 mg/L of $CaCl_2$, pH: 7.3).

20 mL of an inorganic salt medium containing 100 mg-C/L of carbon source was added to a vial of 50 mL in capacity, after which strain N23 was added to 50 mg-cell/L and the sample was cultured under rotary shaking at 28° C., and 120 rpm (n=3). It should be noted that, for the carbon source, 1,4-dioxane, glyoxylic acid, glycolic acid, glyoxal, ethylene glycol, diethylene glycol, triethylene glycol, 1,4-butanediol, 1-butanol, phenol, tetrahydrofuran, glucose, and acetic acid were used, respectively.

Figure 10:
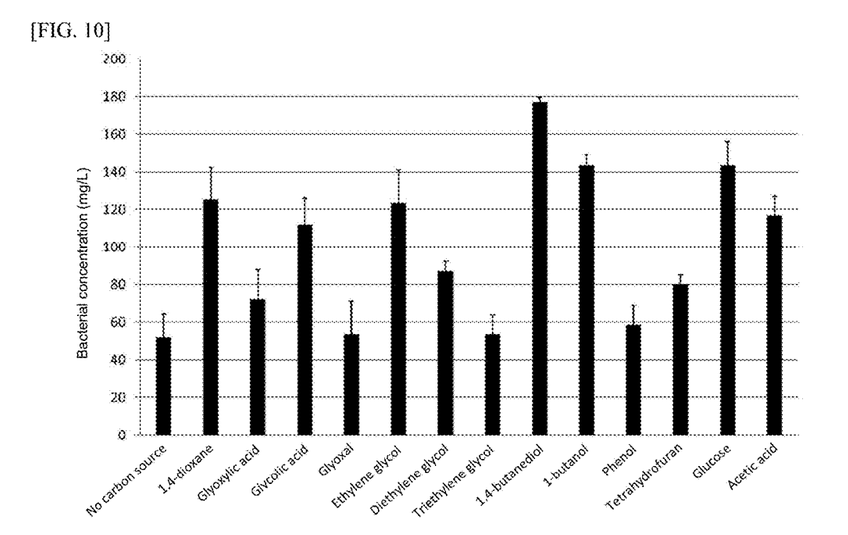
FIG. 10 Graph showing the bacterial cell concentrations at the end of culturing, by carbon source, in Example 8.
Figure 11:
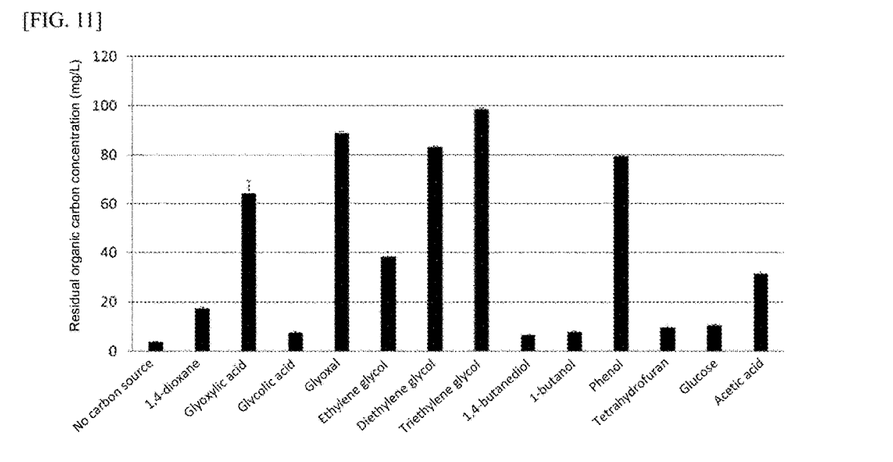
FIG. 11 Graph showing the residual organic carbon concentrations at the end of culturing, by carbon source, in Example 8.

After seven days of culturing, solid contents in the culture solution were recovered using a glass fiber filter (GF/B, Whatman, diameter 47 mm), which were then dried at 105° C. to measure the bacterial cell concentration. Also, the total concentration of organic carbon residues in the solution recovered by filtering, was measured using a TOC meter. It should be noted that a control system to which no carbon source was added was also tested in the same manner for comparison. FIG. 10 shows the bacterial cell concentrations, while FIG. 11 shows the residual organic carbon concentrations.

After seven days of culturing, the bacterial cell concentrations rose considerably, except in the experiments using glyoxal, triethylene glycol, and phenol. In particular, high bacterial cell concentrations were shown when 1,4-dioxane, 1,4-butanediol, 1-butanol, and glucose were used. Also, the values of residual organic carbon concentrations were low in the experimental systems where clear bacterial growth was confirmed. Based on the above results, strain N23 can be grown using 1,4-dioxane, glyoxylic acid, glycolic acid, ethylene glycol, diethylene glycol, 1,4-butanediol, 1-butanol, tetrahydrofuran, glucose, and acetic acid, as carbon sources. This means that strain N23 can be cultured efficiently using these carbon sources.

[Sequence Listing]

PCT_Constitutive 1,4-Diox_20160407_120140_2.txt

What is claimed is:

1. A suspension containing:
    a constitutive 1,4-dioxane-degrading bacteria which is strain N23 deposited as Accession No. NITE BP-02032; and
    one or more elements selected from the group consisting of 1,4-dioxane, glyoxylic acid, glycolic acid, ethylene glycol, diethylene glycol, 1,4-butanediol, 1-butanol, tetrahydrofuran, glucose, and acetic acid.

2. The suspension according to claim 1, wherein a total concentration of the one or more elements is $1.0 \times 10^{-8}$ percent by weight or more but no more than 10.0 percent by weight.

3. The suspension according to claim 1, wherein a total sum of the one or more elements is 60 percent by weight or more relative to a total quantity of organic compounds in the suspension.

4. The suspension according to claim 1, wherein the one or more elements are at least one of 1,4-dioxane, ethylene glycol, diethylene glycol, or 1,4-butanediol.

5. The suspension according to claim 1, wherein a total sum of 1,4-dioxane, ethylene glycol, diethylene glycol, and 1,4-butanediol is 60 percent by weight or more relative to a total quantity of organic compounds in the medium.

6. The suspension according to claim 1, further contains at least one compound selected from the group consisting of $K_2HPO_4$, $(NH_4)_2SO_4$, $MgSO_4 \cdot 7H_2O$, $FeC_{13}$, $CaCl_2$), and NaCl.

7. The suspension according to claim 1, further contains at least one component selected from the group consisting of corn steep liquor, casamino acid, yeast extract, and peptone.

* * * * *

UNITED STATES PATENT AND TRADEMARK OFFICE
CERTIFICATE OF CORRECTION

PATENT NO.          : 10,329,631 B2
APPLICATION NO.     : 15/573401
DATED               : June 25, 2019
INVENTOR(S)         : Norifumi Yamamoto, Yuji Saito and Hironori Taki It is certified that error appears in the above-identified patent and that said Letters Patent is hereby corrected as shown below:

In the Claims

At Column 17, Line 27, in Claim 6, please delete "MgSO4.7H2O" and insert therefor --MgSO4•7H2O--

At Column 17, Line 27, in Claim 6, please delete "FeC13" and insert therefor --FeCl3--

At Column 17, Line 27, in Claim 6, please delete "CaCl2)" and insert therefor --CaCl2--

Signed and Sealed this
Twenty-ninth Day of October, 2019

Andrei Iancu
*Director of the United States Patent and Trademark Office*